United States Patent [19]
Flashinski et al.

[11] Patent Number: 4,774,082
[45] Date of Patent: Sep. 27, 1988

[54] VOLATILE INSECT REPELLENTS

[75] Inventors: Stanley J. Flashinski; John H. Hainze; Calvin J. Verbrugge, all of Racine County, Wis.

[73] Assignee: S. C. Johnson & Son, Inc., Racine, Wis.

[21] Appl. No.: 2,903

[22] Filed: Jan. 13, 1987

[51] Int. Cl.$^4$ .............................................. A61K 31/78
[52] U.S. Cl. .............................. 424/78; 424/DIG. 10; 514/919
[58] Field of Search ...................... 424/78, 81, 83, 405, 424/DIG. 10; 514/919

[56] References Cited

U.S. PATENT DOCUMENTS

| | | | |
|---|---|---|---|
| 2,808,359 | 10/1957 | Schmutzler | 514/533 |
| 2,884,355 | 4/1959 | Goodhue et al. | 514/354 |
| 3,860,700 | 1/1975 | Viout et al. | 514/938 X |
| 3,966,902 | 6/1976 | Chromecek | 424/78 X |
| 4,358,573 | 11/1982 | Verbrugge | 526/272 |
| 4,388,352 | 6/1983 | Allan et al. | 424/401 X |
| 4,435,383 | 3/1984 | Wysong | 424/78 |
| 4,489,056 | 12/1984 | Himmelstein et al. | 424/486 |
| 4,512,969 | 4/1985 | Chen | 424/78 X |
| 4,548,764 | 10/1985 | Munteanu et al. | 261/75 |
| 4,657,759 | 4/1987 | Hansen et al. | 424/83 |
| 4,663,346 | 5/1987 | Coulston et al. | 514/456 |
| 4,693,890 | 9/1987 | Wilson | 424/78 |
| 4,747,902 | 5/1988 | Saitoh | 156/244.11 |

OTHER PUBLICATIONS

Mehr et al., J. Am. Mosq. Control Assoc., 1(2): 143-147, (Jun., 1985), Laboratory Evaluation of Controlled-Release Insect Repellent Formulations.

Randall & Brower, J. Med. Entomol, 23(3): 251-255, (May 1986), A New Method to Determine Repellent, Neutral, or Aggregative Properties of Chemicals on *Blattella germanica* (Dictyoptera: Blattellidae).

Primary Examiner—John F. Terapane
Assistant Examiner—Catherine S. Kilby

[57] ABSTRACT

This invention relates to volatile insect repellent compositions comprising an insect repellent, such as deet, and specific maleic anhydride/alpha olefin polymers to increase the residual activity of the insect repellent.

30 Claims, No Drawings

VOLATILE INSECT REPELLENTS

BACKGROUND OF THE INVENTION

This application is related to a copending application entitled "Contact Insect Repellents" and filed concurrently herewith.

This invention relates to new and useful compositions of matter suitable as volatile insect repellents. More particularly, this invention relates to the use of maleic anhydride/alpha olefin polymers to increase the residual activity of volatile insect repellents.

Insect repellents have historically been selected on the basis of their persistence on the skin. Unfortunately, the usual topically applied insect repellents, such as diethyl toluamide, are fairly volatile, and therefore, have the disadvantage of giving protection only for relatively short periods of time due to their rapid evaporation and/or absorption by the skin. Both problems, absorption and evaporation, necessitate frequent applications which are bothersome and time consuming.

Adding adjuvant materials to increase the persistence of insect repellents was reported as early as 1928 for a formula consisting of oil of citronella, spirits of camphor, oil of tar, oil of pennyroyal and castor oil. Mehr et al., Laboratory Evaluation of Controlled-Release Insect Repellent Formulations, *J. Am. Mosq. Control Assoc.*, Vol. 1(2):143 (June, 1985). The Mehr et al. researchers tested the persistence of several controlled-release formulations of diethyl toluamide, or more specifically, N,N-diethyl-3-methylbenzamide. Diethyl toluamide is commonly known as deet. These formulations consisted of microcapsule and free-repellent formulations containing hydrophilic vinyl polymers, such as polyvinylpyrrolidone.

U.S. Pat. No. 2,808,359 discloses that absorption by the skin and evaporation are reduced by mixing insect repellents with hydroxyalkyl esters of dicarboxylic acids, including bis(2-ethyl-3-hydroxy-hexyl) maleate. Other patents also disclose the use of various materials to extend the residual activity of insect repellents or slow release pesticides. See, for example, U.S. Pat. Nos. 2,884,355, 4,435,383 and 4,489,056.

U.S. Pat. No. 4,358,573 teaches that maleic anhydride/alpha olefin terpolymers are useful as mold release agents, slip agents and additives to floor polishes. They are not said to increase the residual activity of volatile insect repellents.

Accordingly, a long-standing need exists to provide an insect repellent composition for topical and/or surface application with improved residual activity, i.e., the period of repellent activity after application.

Deet, as well as other insect repellents, exhibit a greasy "feel" when applied to the skin. Accordingly, a need exists to improve the tactile "feel" of deet and other repellents in topically applied compositions.

SUMMARY OF THE INVENTION

In a first embodiment, this invention relates to volatile insect repellent compositions having enhanced residual insect repellent activity comprising: (1) at least one volatile insect repellent; and (2) at least one polymer consisting of (a) about 49-60 mole percent maleic anhydride, and (b) about 51-40 mole percent of at least one 1-alkene having 4-30 carbon atoms, wherein the weight ratio of insect repellent to polymer is from about 10:1 to 50:1. Additionally, this invention relates to a method of repelling insects utilizing these polymer-containing volatile insect repellent compositions.

In a second embodiment, this invention includes compositions having enhanced residual insect repellency comprising: (1) at least one volatile insect repellent; and (2) at least one polymer consisting of (a) about 49-60 mole percent maleic anhydride, (b) about 10-40 mole percent of at least one 1-alkene having from 4-16 carbon atoms, and (c) about 10-40 mole percent of at least one 1-alkene having from 18-30 carbon atoms, wherein the weight ratio of insect repellent to polymer is from about 10:1 to 50:1. Unless stated otherwise, references to mole percents are based on the total weight of the polymer.

In still further embodiments, the above compositions may optionally contain various alcohols, such as the lower alkanols, ethanol and the like, or other solvents and/or propellants, if an aerosol formulation is desired.

It is believed that the compositions of the present invention and the method of using them unexpectedly prolong residual activity by reducing skin absorption and evaporation of the insect repellent.

It has been found that the compositions of the invention unexpectedly produce better repellency, i.e., they prolong the protection from mosquitoes and flies as compared with those formulations not containing a polymer of the invention.

It has also been unexpectedly found that the addition of a maleic anhydride/alpha olefin polymer to the insect repellent, deet, not only improves residual activity, but also the tactile characteristics of the deet formulation as applied to the skin.

DESCRIPTION OF THE PREFERRED EMBODIMENTS

The volatile insect repellents that may be utilized in accordance with the teachings of this invention are those considered effective against the particular insect targeted, and preferably, those compatible with the skin for topical applications.

Examples of volatile insect repellents effective against mosquitoes and biting flies include: N,N diethyl toluamide (deet); ethyl hexanediol; 2-(octyl thio) ethanol; dimethyl phthalate; di-n-propyl-2,5-pyridine dicarboxylate; 1,5a,6,9,9a,9b-hexahydro-4a(4h)-dibenzofuran carboxaldehyde; citronellal (3,7-dimethyl-6-octenal); citronellol (3,7-dimethyl-6-octen-1-ol); geraniol (trans-3,7-dimethyl-2,6-octadien-1-ol); nerol (cis-3,7-dimethyl-2,6-octadien-1-ol); linalool (3,7-dimethl-1,6-octadien-3-ol); and mixtures thereof.

The concentration of repellent utilized in accordance with the teachings of this invention is not critical. The lower limit is defined by that amount required to form an effective dosage, and the upper limit, by economic considerations. The amount of insect repellent employed will vary depending on several factors, including, the type of insect repellent, the targeted insect or insects, and the other ingredients utilized, e.g., the maleic anhydride polymer.

The concentration of insect repellent can preferably be from about 1% to 90%, based on the total weight of the insect repellent composition. The preferred ranges are from about 1 to 25 percent, based on the total weight of the insect repellent composition. Unless otherwise indicated, all percentages of ingredients are calculated as weight percentages based on the total weight of the insect repellent composition.

Other insect repellents, especially those well known in the art and useful for such purposes, can also be readily utilized.

Maleic anhydride/alpha olefin polymers may be utilized, in accordance with the teachings of this invention, to increase insect residual activity. These polymers include compositions having (a) about 49 to 60 mole percent maleic anhydride and (b) about 51 to 40 mole percent of at least one 1-alkene having from 4–30 carbon atoms. Preferred maleic anhydride polymers have (a) about 49–55 mole percent maleic anhydride and (b) about 45–51 mole percent of at least one 1-alkene having from 6–16 carbon atoms (e.g. 1-decene), with 8–12 carbon atoms being more preferred. A more preferred polymer has about 50 mole percent maleic anhydride and about 50 mole percent 1-decene.

Additional polymers that may be utilized in accordance with the teachings of this invention include the maleic anhydride/alpha olefin terpolymers disclosed in U.S. Pat. No. 4,358,573. which is incorporated herein by reference. These are formed from monomers comprising: (a) about 49–60 mole percent maleic anhydride, (b) about 10–40 mole percent of a least one 1-alkene having from 4–16 carbon atoms, and (c) about 10–40 mole percent of at least one 1-alkene having from 18–30 carbon atoms.

Additionally, preferred maleic anhydride/alpha olefin polymers include: (a) about 49 to 55 mole percent maleic anhydride, (b) about 20 to 30 mole percent of at least one 1-alkene having from 8–12 carbon atoms (e.g. 1-decene), and (c) about 20–30 mole percent of at least one 1-alkene having from 18–24 carbon atoms (1-octadecene; and also (a) about 49–55 mole percent maleic anhydride, (b) about 20–30 mole percent of at least one 1-alkene having from 8–12 carbon atoms, and (c) about 20–30 mole percent of a mixture of 1-alkenes consisting of about 45–55 mole percent 1-eicosene, about 40–55 mole percent 1-docosene, and about 5–10 mole percent 1-tetracosene.

The maleic anhydride/alpha olefin polymers are generally present in amounts sufficient to reduce the evaporation and skin absorption of the insect repellent. Accordingly, these materials may be present in amounts from about 0.1 to 25 percent, based on the total weight of the insect repellent composition, with preferred amounts ranging from about 1 to 5 percent.

It has been discovered, however, that the concentration of polymer is dependent on the concentration of insect repellent. Accordingly, a weight ratio of insect repellent to polymer from about 10:1 to 50:1 is desirable to attain the objectives of this invention. A weight ratio of 15:1 to 25:1 is more preferred. The particular ratio selected is of course, dependent on the repellent, its volatility and the polyme utilized. If the ratio of repellent to polymer is less than about 10:1, the polymer may tightly bind the volatile repellent, thereby preventing its release and repellent effect. If the ratio is greater than about 50:1, the repellent will usually be released too rapidly and the composition will rapidly lose it residual activity.

The application of these compositions is facilitated by solution of the active ingredients in solvents, such as the lower alkanols, ethanol and the like, kerosene and similar petroleum oils, ethers, ketones, aldehydes, and the like.

Additionally, the compositions of the present invention may be applied in aerosol form, in which case, the above-identified compositions may additionally contain a propellent or a mixture of propellents. The type of propellent is not critical, and any of those conventionally utilized can be employed to produce an aerosol formula. Typical propellents include isobutane, propane, n-butane, and the like, and mixtures thereof, which are utilized in conventional amounts.

In preparing the compositions of this invention, the insect repellent is generally added directly to an alcoholic polymer solution which can then be formulated or packaged in any form commonly used for such repellents, i.e., aerosol, pump spray, roll-on or lotion. It is clear to those skilled in the art that the anhydride group of the polymer is converted to the half alkyl ester under these conditions, i.e., the presence of alcohol at room temperature.

In each of the following formulations, $MA_N$=maleic anhydride. The number or numerical range preceding $MA_N$ is the mole percent of maleic anhydride in the polymer. The group $C_x$-$C_{x'}$ denotes the number of carbon atoms comprising the 1-alkene. The number or numerical range preceding this designation is the mole percent of the 1-alkene in the polymer.

Typical preparations of this invention include:

| Ingredients | Amount (percent by weight) Preferred | More Preferred |
|---|---|---|
| General Formula | | |
| Insect repellant | 1–90 | 1–25 |
| Polymer | 0.1–25 | 0.1–1.5 |
| Carrier/propellant | 0–99 | 73.5–99 |

| Ingredients | Amount (percent by weight) | Repellent: Polymer Ratio |
|---|---|---|
| Formula 1 | | |
| Deet | 5–50 | 10:1 to 50:1 |
| 49-60 $MA_N$/51-40 $C_8$-$C_{12}$ | 0.5–5 | |
| Carrier/propellent | 45–95 | |
| Formula 2 | | |
| Deet | 10–20 | 15:1 to 25:1 |
| 49-60 $MA_N$/51-40 $C_8$-$C_{12}$ | 0.1–2 | |
| Carrier/propellent | 78–90 | |
| Formula 3 | | |
| Deet | 15 | 15:1 |
| 50 $MA_N$/50 $C_{10}$ | 1 | |
| Carrier/propellent | 84 | |
| Formula 4 | | |
| Deet | 5–50 | 10:1 to 50:1 |
| 49-55 $MA_N$/20-30 $C_8$-$C_{12}$ 20-30 $C_{18}$-$C_{24}$ | 0.5–5 | |
| Carrier/propellent | 45–95 | |
| Formula 5 | | |
| Deet | 10–20 | 15:1 to 25:1 |
| 49-55 $MA_N$/20-30 $C_8$-$C_{12}$ 20-30 $C_{18}$-$C_{24}$ | 0.1–2 | |
| Carrier/propellent | 78–90 | |
| Formula 6 | | |
| Deet | 15 | 15:1 |
| 50 $MA_N$/25 $C_{10}$ 25 $C_{18}$ | 1 | |
| Carrier/propellent | 84 | |
| Formula 7 | | |
| Deet | 5–50 | 10:1 to 50:1 |
| 49-55 $MA_N$/20-30 $C_8$-$C_{12}$ 20-30 $C_{20}$-$C_{24}$ | 0.5–5 | |
| Carrier/propellent | 45–95 | |
| Formula 8 | | |
| Deet | 10–20 | 15:1 to 25:1 |
| 49-55 $MA_N$/20-30 $C_8$-$C_{12}$ 20-30 $C_{20}$-$C_{24}$* | 0.1–2 | |
| Carrier/propellent | 78–90 | |
| Formula 9 | | |
| Deet | 15 | 15:1 |
| 49-55 $MA_N$/25 $C_{10}$ | 1 | |

| -continued | | |
|---|---|---|
| 25 $C_{20}$–$C_{24}$** | | |
| Carrier/propellent | 84 | |
| | Formula 10 | |
| Deet | 10–20 | 15:1 |
| 49-55 $MA_N$/20-30 $C_{8-12}$ | 0.1–2 | |
| 20-30 $C_{24-30}$ | | |
| Carrier/propellent | 78–90 | |

*The $C_{20}$–$C_{24}$ 1-alkenes comprise 45–55 mole percent $C_{20}$, 40–50 mole percent $C_{22}$ and 5–10 mole percent $C_{24}$.
**The $C_{20}$–$C_{24}$ 1-alkenes comprise 50.1 mole percent $C_{20}$, 43.4 mole percent $C_{22}$ and 6.5 mole percent $C_{24}$.

In order to illustrate the improved results obtained from the present invention, repellency tests were conducted to show the improvements in residual activity provided by the volatile insect repellent compositions of the present invention. These tests, which illustrate the scope of the invention but do not limit it, were carried out in the following manner:

EXAMpLE 1

The compositions of this invention having the formulations set forth in Table 1 were prepared by mixing an alcohol solution of the polymer with deet and a propellent consisting of 75% isobutane and 25% butane, and packaging this formulation in standard aerosol cans.

The formulations were tested for their residual repellent activity against mosquitoes and flies for lands and bites as follows: The test insects were adults, reared on 10% sucrose solutions, consisting of (1) about 6,000 mixed sex stable flies, *Stomoxys calcitrans*, three weeks from peak emergence, or (2) about 4,000 mixed sex mosquitoes, *Aedes aegypti*, seven days from peak emergence, that were separately placed in screened wooden cages. A test subject's forearm was thoroughly cleaned, treated with the repellent material at a rate of 1 gram or 2 ml per 645 square cm. from the wrist to the elbow, and then exposed to the test insects at pre-determined time intervals, usually one minute every 30 minutes, with the first exposure at 30 minutes after application. The observations noted were for repellency (no landing insects), lands (insect lands, but does not bite), and bites (insect lands and bites). The test was terminated when insect bites were received during two consecutive exposures. The longer the period between application and the time of first land and/or first bite, the more effective the insect repellent, i.e., the greater its residual activity.

The results in Table 1 demonstrate that at least about a 10:1 weight ratio of insect repellent to polymer significantly increases the residual activity of the repellent, as measured by the time for the first mosquito or fly bite to occur, when compared to a control formulation not containing a polymer of this invention.

When the weight ratio deet to polymer was lowered to about 7.5:1, i.e., 15% deet and 2% polymer as in Formula B, the residual activity was somewhat better than a control formulation not containing a polymer of this invention. When the ratio of repellent to polymer was lowered still further to about 5:1 as shown in Formula A, the residual actiiity was inferior to the residual activity of a control formula not containing a polymer. It is believed that with ratios lower than about 10:1, the polymer tightly binds the deet, preventing it from volatilizing, and thereby inhibiting its effectiveness as an insect repellent.

TABLE 1

| Formula | Ingredients and Concentration | Mean Hours of Protection (Time to First Land/Bite in Hours)[3] | | | |
|---|---|---|---|---|---|
| | | Mosquitoes[4] | | Flies[4] | |
| | | Lands | Bites | Lands | Bites |
| Control-1 | 15% deet<br>74.5% ethanol<br>10% propellent[5]<br>0.5% fragrance | 1.5 ± 0.5 | 4.0 ± 1.0 | 1.0 ± 1.0 | 3.5 ± 1.0 |
| A | 15% deet<br>3% polymer-1[1]<br>72% ethanol<br>10% propellent[2] | 1.3 ± 0.1 | 3.7 ± 1.3 | 0.5 ± 0.5 | 3.5 ± 1.0 |
| Control-2 | 15% deet<br>74.5% ethanol<br>10% propellent[5]<br>0.5% fragrance | 1.4 ± 0.4 | 3.9 ± 1.4 | 1.0 ± 0.4 | 1.8 ± 0.3 |
| B | 15% deet<br>2% polymer-1[1]<br>73% ethanol<br>10% propellent[2] | 1.5 ± 0.5 | 4.9 ± 0.8 | 1.1 ± 0.1 | 2.4 ± 0.7 |
| Control-3 | 15% deet<br>74.5% ethanol<br>10% propellent[5]<br>0.5% fragrance | 2.0 ± 0.2 | 4.5 ± 0.6 | 1.1 ± 0.4 | 1.7 ± 0.2 |
| C | 15% deet<br>1% polymer-1[1]<br>74% ethanol<br>10% propellent[2] | 2.4 ± 0.5 | 5.6 ± 0.6 | 1.2 ± 0.3 | 2.4 ± 0.3 |

[1]The polymer consists of about 50 mole percent maleic anhydride, about 25 mole percent 1-decene and about 25 mole percent 1-octadecene.
[2]The formula A, B and C propellent consists of about 75% isobutane and about 25% butane.
[3]Control-1 and Formula A tests were replicated 2 times. Control-2 and Formula B tests were replicated 4 times. Control-3 and Formula C tests were replicated 7 times. The differences between the Control-3 and Formula 3 tests were significant at the 0.05 level for mosquito and fly bites.
[4]*Aedes aegypti* mosquitoes and *Stomoxys calcitrans* flies.
[5]The control-1, 2 and 3 propellent consists of 62% n-butane and 38% propane.

Similar results are obtained when Formulas 1–10 are substituted for the test compositions in Example 1.

It will be recognized by those skilled in this art that various modifications can be made within the overall concept of this invention. For example, skin care additives, skin treating ingredients, and the like can also be added within the scope of this invention.

This invention is not to be limited except as set forth in the following claims.

What is claimed is:

1. A volatile, insect-repellent composition having enhanced residual insect repellent activity, comprising:
    (1) at least one volatile insect repellent; and
    (2) an effective amount of at least one polymer for increasing the residual activity of the volatile insect repellent, said one polymer consisting of:
        (a) about 49–60 mole percent maleic anhydride, and
        (b) about 51–40 mole percent of at least one 1-alkene having 4–30 carbon atoms,
    wherein the weight ratio of insect repellent to polymer is from about 10:1 to 50:1.

2. A composition according to claim 1, wherein the polymer consists of:
    (a) about 49–55 mole percent maleic anhydride, and
    (b) about 45–51 mole percent of at least one 1-alkene having from 6–16 carbon atoms.

3. A composition according to claim 2, wherein the 1-alkene has from 8–12 carbon atoms.

4. A composition according to claim 1, wherein the polymer consists of about 49–55 mole percent maleic anhydride and about 45–51 mole percent of 1-decene.

5. A composition according to claim 1, wherein the polymer has:
    about 10–40 mole percent of at least one 1-alkene having from 4–16 carbon atoms, and about 10–40 mole percent of at least one 1-alkene having from 18–30 carbon atoms.

6. A composition according to claim 1, wherein the polymer consists of:
    (a) about 49–55 mole percent maleic anhydride,
    (b) about 20–30 mole percent of at least one 1-alkene having from 8–12 carbon atoms, and
    (c) about 20–30 mole percent of at least one 1-alkene having from 18–24 carbon atoms.

7. A composition according to claim 1, wherein the polymer consists of:
    (a) about 49–55 mole percent maleic anhydride,
    (b) about 20–30 mole percent 1-decene, and
    (c) about 20–30 mole percent 1-octadecene.

8. A composition according to claim 1. wherein the polymer consists of:
    (a) about 49–55 mole percent maleic anhydride,
    (b) about 20–30 mole percent of at least one 1-alkene having from 8–12 carbon atoms, and
    (c) about 20–30 mole percent of a mixture of 1-alkenes consisting of about 45–55 mole percent 1-eicosene, about 40–55 mole percent 1-docosene, and about 5–10 mole percent 1-tetracosene.

9. A composition according to claim 1. wherein the volatile insect repellent is selected from the group consisting of N,N-diethyl toluamide; ethyl hexanediol; 2-(octylthio) ethanol; dimethyl phthalate; di-n-propyl-2,5-pyridine dicarboxylate; 1,5a, 6, 9, 9a. 9b-hexahydro-4a(4h)-dibenzofuran carboxaldehyde; citronellal; citronellol; geraniol; nerol; linalool; and mixtures thereof.

10. A composition according to claim 1, wherein the inset repellent is N,N-diethyl toluamide.

11. A composition according to claim 1, wherein the volatile insect repellent is N,N-diethyl toluamide and the polymer consists of about 50 mole percent maleic anhydride and about 50 mole percent 1-decene.

12. A volatile, insect-repellent composition having enhanced residual insect repellent activity, comprising:
    (1) at least one volatile insect repellent;
    (2) an effective amount of at least one polymer for increasing the residual activity of the volatile insect repellent, said one polymer consisting of:
        (a) about 49–60 mole percent maleic anhydride, and
        (b) about 51–40 mole percent of at least one 1-alkene having 4–30 carbon atoms, wherein the weight ratio of insect repellent to polymer is from about 10:1 to 50:1; and
    (3) a lower alkanol.

13. A composition according to claim 12, wherein the polymer has:
    about 10–40 mole percent of at least one 1-alkene having from 4–16 carbon atoms, and about 10–40 mole percent of at least one 1-alkene having from 18–30 carbon atoms.

14. A composition according to claim 1, further comprising a solvent.

15. A composition according to claim 1, further comprising a propellent.

16. A method for repelling insects, comprising applying a volatile insect repellent composition to an area to be made repellent, said composition having enhanced residual insect repellent activity and comprising:
    (1) at least one volatile insect repellent; and
    (2) an effective amount of at least one polymer for increasing the residual activity of the volatile insect repellent, said one polymer consisting of:
        (a) about 49–60 mole percent maleic anhydride, and
        (b) about 51–40 mole percent of at least one 1-alkene having 4–30 carbon atoms. wherein the weight ratio of insect repellent to polymer is about 10:1 to 50:1.

17. A method according to claim 16, wherein the polymer consists of:
    (a) about 49–55 mole percent maleic anhydride, and
    (b) about 45–51 mole percent of at least one 1-alkene having from 6–16 carbon atoms.

18. A method according to claim 17, wherein the 1-alkene has from 8–12 carbon atoms.

19. A method according to claim 16, wherein the polymer consists of about 49–55 mole percent maleic anhydride and about 45–51 mole percent of 1-decene.

20. A method according to claim 16, wherein the polymer has:
    about 10–40 mole percent of at least one 1-alkene having from 4–16 carbon atoms, and about 10–40 mole percent of at least 1-alkene having from 18–30 carbon atoms.

21. A method according to claim 16, wherein the polymer consists of:
    (a) about 49–55 mole percent maleic anhydride,
    (b) about 20–30 mole percent of at least one 1-alkene having from 8–12 carbon atoms, and
    (c) about 20–30 mole percent of at least one 1-alkene having from 18–24 carbon atoms.

22. A method according to claim 16 wherein the polymer consists of:
    (a) about 49–55 mole percent maleic anhydride,
    (b) about 20–30 mole percent 1-decene, and
    (c) about 20–30 mole percent 1-octadecene.

23. A method according to claim 16, wherein the polymer consists of:
    (a) about 49–55 mole percent maleic anhydride,
    (b) about 20–30 mole percent of at least one 1-alkene having from 8–12 carbon atoms, and (c) about 20-30 mole percent of a mixture of 1-alkenes consisting! of about 45-55 mole percent 1-eicosene, about 40-55 mole percent 1-docosene, and about 5-10 mole percent 1-tetracosene.

24. A method according to claim 16, wherein the volatile insect repellent is selected from the group consisting of N.N-diethyl toluamide; ethyl hexanediol; 2-(octyl thio) ethanol; dimethyl phthalate; di-n-propyl-2,5-pyridine dicarboxylate; 1,5a, 6, 9, 9a, 9b-hexahydro-4a(4h)-dibenzofuran carboxaldehyde; citronellal; citronellol; geraniol; nerol; linalool; and mixtures thereof.

25. A method according to claim 16, wherein the insect repellent is N,N-diethyl toluamide.

26. A method according to claim 16, wherein the volatile insect repellent is N,N-diethyl toluamide and the polymer consists of about 50 mole percent maleic anhydride and about 50 mole percent 1-decene.

27. A method for repelling insects, comprising applying a volatile insect repellent composition to an area to be made repellent, said composition having enhanced residual repellent activity and comprising:

(1) at least one volatile insect repellent; and
(2) an effective amount of at least one polymer for increasing the residual activity of the volatile insect repellent, said one polymer consisting of:
  (a) about 49-60 mole percent maleic anhydride, and
  (b) about 51-40 mole percent of at least one 1-alkene having 4-30 carbon atoms, wherein the weight ratio of insect repellent to polymer is about 10:1 to 50:1; and
  (c) a lower alkanol.

28. A method according to claim 27, wherein the polymer has:
  about 10-40 mole percent of at least one 1-alkene having from 4-16 carbon atoms, and about 10-40 mole percent of at least one 1-alkene having from 18-30 carbon atoms.

29. A method according to claim 16, further comprising a solvent.

30. A method according to claim 16, further comprising a propellent.

* * * * *